(12) United States Patent
Plisson

(10) Patent No.: US 7,560,453 B2
(45) Date of Patent: Jul. 14, 2009

(54) 6-(2, 3, 4, 5-TETRAHYDRO-1H-BENZO [D] AZEPIN-7-YLOXY)-NICOTAMIDE DERIVATIVES AS RADIO LABELLED LIGANDS

(75) Inventor: Christophe Plisson, Cambridge (GB)

(73) Assignee: Glaxo Group Limited, Greenford, Middlesex (GB)

( * ) Notice: Subject to any disclaimer, the term of this patent is extended or adjusted under 35 U.S.C. 154(b) by 2 days.

(21) Appl. No.: 11/813,357

(22) PCT Filed: Jan. 5, 2006

(86) PCT No.: PCT/EP2006/000112

§ 371 (c)(1),
(2), (4) Date: Jul. 5, 2007

(87) PCT Pub. No.: WO2006/072596

PCT Pub. Date: Jul. 13, 2006

(65) Prior Publication Data

US 2008/0166298 A1    Jul. 10, 2008

(30) Foreign Application Priority Data

Jan. 7, 2005 (GB) ................................ 0500283.7
Jan. 12, 2005 (GB) ................................ 0500592.1

(51) Int. Cl.
*A61P 25/28* (2006.01)
*A61K 31/55* (2006.01)
*C07D 223/16* (2006.01)
(52) U.S. Cl. .................................. 514/217.01; 540/594
(58) Field of Classification Search ............ 514/217.01; 540/594
See application file for complete search history.

(56) References Cited

FOREIGN PATENT DOCUMENTS

WO    2004/056369    7/2004
WO    2005/014479    2/2005

OTHER PUBLICATIONS

J. M. Arrang, M. Garbarg and J.-C. Schartz. Auto-inhibition of brain histamine release mediated by a novel class ($H_3$) of histamine receptor. Nature 1983, 302, 832-837.
J. Clapham and G. J. Kilpatrick. Histamine $H_3$ receptors modulate the release of [$^3$H]acetylcholine from slices of rat entorhinal cortex—evidence of the possible existence of $H_3$ receptors subtypes. Br. J. Pharmacol. 1992, 107, 919-923.
E. Schlicker, K. Fink, M. Hinterthaner and M Goethert. Inhibition of noradrenaline release in the rat brian cortex via presynaptic $H_3$ receptors. Naunyn-Schmiedberg's Arch. Pharmacol. 1989, 340, 633-638.
E. Schlicker, K. Fink, M. Detzner, M. Gothert. Histamine inhibits dopamine release in the mouse striatum via presynaptic $H_3$ receptors. Journal of neural transmission. General section 1993, 93, 1-10.
K. Fink, E. Schlicker, A. Neise, M. Gothert. Involvement of presynaptic $H_3$ receptors in the inhibitory effect of histamine on serotonin release in the rat brain cortex. Naunyn-Schmiedeberg's archives of pharmacology 1990, 342, 513-519.
A. A. Rodrigues, F. P. Jansen, R. Leurs, H. Timmerman, G. D. Prell. Interaction of clozapine with the histamine $H_3$ receptor in rat brain. Br. J. Pharmacol. 1995, 114, 1523-1524.
R. Leurs, P. Blandina, C. Tedford and H. Timmerman. Therapeutic potential of histamine $H_3$ receptor agonists and antagonists. Trends in Pharmacological Sciences 1998, 19, 177-183.
G. A. Bray and L. A. Tartaglia. Medicinal strategies in the treatment of obesity. Nature 2000, 404, 672-677.
L. F. Alguacil and C. Perez-Garcia. Histamine $H_3$ receptor: A potential drug target for the treatment of central nervous system disorders. Current Drug Targets: CNS & Neurological Disorders 2003, 2, 303-313.
C. Pillot, J. Ortiz, A. Heron, S. Ridray, J.-C. Schwartz and J.-M. Arrang. Ciproxifan, histamine $H_3$-receptor antagonist/inverse agonist, potentiates neurochemicals and behavioural effects of haloperidol in the rat. J. Neurosci. 2002, 22, 7272-7280.
E. Mignot, S. Taheri and S. Nishino. Sleeping with the hypothalamus: emerging therapeutics targets for sleep disorders. Nature Neurosci. 2002, 5, 1071-1075.
J.-M. Arrang, M. Garbarg, J.-C. Lancelot, J.-M. Lecomte, H. Pollard, M. Robba, W. Schunack and J.-C. Schwartz. Highly potent and selective ligands for histamine $H_3$-receptors. Nature 1987, 327, 111-123.
M. Kathmann, E. Schlicker, I. Marr, S. Werthwein, H Stark and W. Schunack. Ciproxifan and chemically related compounds are highly potent and selective histamine $H_3$-receptor antagonists. Naunyn-Schmiedeberg's Arch Pharmacol 1998, 358, 623-627.
H. Stark, B. Sadek, M. Krause, A. Huls, X. Ligneau, C. Robin Ganellin, J.-M. Arrang, J.-C. Schwartz and W. Schunack. J. Med. Chem. 2000, 43, 3987-3997.
X. Ligneau, J.-S. Lin, G. Vanni-Mercier, M. Jouvet, J. L. Muir, C. R. Ganellin, H. Stark, S. Elz, W. Schunack and J.-C. Schwartz. Neurochemical and behavioural effects of Ciproxifan, a potent histamine H3-receptor antagonist. J. Pharmacol. Exp. Ther. 1998, 287, 658-666.

(Continued)

*Primary Examiner*—Brenda L Coleman
(74) *Attorney, Agent, or Firm*—Bonnie L. Deppenbrock

(57) ABSTRACT

The present invention relates to radiolabelled compounds of formula (I), which are useful for the labelling and diagnostic imaging of histamine $H_3$ receptor functionality.

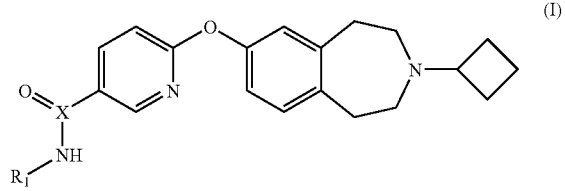

5 Claims, No Drawings

OTHER PUBLICATIONS

H. Stark, K. Purand, A. Huels, X. Ligneau, M. Garbarg, J-C. Schwartz, W. Schunack. [$^{125}$I]Iodoproxyfan and related compounds: A reversible radioligand and novel classes of antagonists with high affinity and selectivity for the histamine $H_3$ receptor. Journal of Medicinal Chemistry 1996, 39, 1220-1226.

A. D. Windhorst, H. Timmerman, R. P. Klok, F. G. J. Custers, W. M. P. B. Menge, R. Leurs, H. Stark, W. Schunack, E. G. J. Gielen, M. J. P. G. van Kroonenburgh and J. D. M. Herscheid. Radiosynthesis and biodistribution of $^{123}$I-labeled antagonists of the histamine $H_3$ receptor as potential SPECT ligands. Nuc. Med. Biol. 1999, 26, 651-659.

A. D. Windhorst, H. Timmerman, R. P. Klok, W. M. P. B. Menge, R. Leurs, and J. D. M. Herscheid. Evaluation of [$^{18}$F]VUF 5000 as a potential PET ligand for brain imaging of the histamine $H_3$ receptor. Bioorg. and Med. Chem. 1999, 7, 1761-1767.

M. Ponchant, S. Demphel, C. Fuseau, C. Coulomb, M. Bottleander, J.-C. Schwartz, H. Stark, W. Schunack, S. Athmani, C. R. Ganellin and C. Crouzel. Radiosynthesis and biodistribution of two potential antagonists of cerebral histamine $H_3$ receptors for PET studies: [$^{18}$F]FUB272 and [$^{11}$C]UCL1829. Abstract of Papers, XIIth International symposium on Radiopharmaceutical Chemistry 1997, Uppsala, Sweden.

6-(2, 3, 4, 5-TETRAHYDRO-1H-BENZO [D] AZEPIN-7-YLOXY) -NICOTAMIDE DERIVATIVES AS RADIO LABELLED LIGANDS

This application is filed pursuant to 35 U.S.C. § 371 as a United States National Phase Application of International Patent Application Serial No. PCT/EP2006/000112 filed Jan. 5, 2006, which claims priority from Great Britain Application No. 0500283.7 filed in the United Kingdom on Jan. 7, 2005, and Great Britain Application No. 0500592.1 filed Jan. 12, 2005, the contents of which are incorporated herein by reference.

The present invention relates to radiolabelled ligands for the histamine $H_3$ receptor, useful for the labelling and diagnostic imaging of the histamine $H_3$ receptor functionality.

It is well established that histamine acts as a neurotransmitter via three distinct histamine receptor subtypes, $H_1$, $H_2$ and $H_3$. The histamine $H_3$ receptor has been reported to play a role as a regulating receptor-system controlling not only the release and synthesis of histamine[1] but also the release of other neurotransmitters, such as acetylcholine,[2] noradrenaline,[3] dopaminergic[4] and serotonergic[5] systems.

Noninvasive, nuclear imaging techniques can be used to obtain basic and diagnostic information about the physiology and biochemistry of living subjects, including experimental animals, patients and volunteers. These techniques rely on the use of imaging instruments that can detect radiation emitted from radiotracers administered to living subjects. The information obtained can be reconstructed to provide planar and tomographic images which reveal the distribution and/or concentration of the radiotracer as a function of time.

Positron emission tomography (PET) is a noninvasive imaging technique that offers the highest spatial and temporal resolution of all nuclear medicine imaging modalities and has the added advantage that it can allow for true quantitation of tracer concentrations in tissues. The technique involves the use of radiotracers, labelled with positron emitting radionuclides, that are designed to have in vivo properties which permit measurement of parameters regarding the physiology or biochemistry of a variety of processes in living tissue.

Compounds can be labelled with positron or gamma emitting radionuclides. The most commonly used positron emitting radionuclides are $^{15}O$, $^{13}N$, $^{11}C$ and $^{18}F$, which are accelerator produced and have half lifes of 2, 10, 20 and 110 minutes respectively. The most widely used gamma emitting radionuclides are $^{18}F$, $^{99m}Tc$, $^{201}Tl$ and $^{123}I$.

$H_3$ receptor ligands have been described such as thioperamide,[6] FUB372,[7] ciproxifan[8] and radioligands such as [$^{125}I$]iodoproxifan[9] developed for in vitro binding studies. PET and SPECT radiolabelled compounds have also been reported e.g. [$^{123}I$]iodoproxifan,[10] [$^{123}I$]GR190028,[10] [$^{123}I$]FUB271,[10] [$^{18}F$]VUF5000,[11] [$^{11}C$]UCL1829[12] and [$^{18}F$]FUB272.[12]

However, none of these radiolabelled compounds have been shown to allow in vivo imaging of histamine $H_3$ receptors in the brain due to low brain uptake (e.g. [$^{123}I$] GR190028, [$^{123}I$]FUB271, [$^{18}F$]FUB, [$^{11}C$]UCL, [$^{18}F$] VUF5000), homogenous brain distribution (e.g. [$^{18}F$]FUB, [$^{11}C$]UCL) and/or no significant alteration of the brain distribution by selective $H_3$ receptor ligand (e.g. [$^{123}I$]iodoproxifan, [$^{18}F$]VUF5000).

WO2004/056369A1[13] discloses a series of benzodiazepine derivatives said to be histamine $H_3$ receptor antagonists and claimed to be useful in the treatment of various neurological disorders. When Example 121 of WO2004/056369A1 is radiolabelled it has been found to allow in vivo imaging of $H_3$ receptors in the brain.

Accordingly the present invention provides a compound of formula (I):

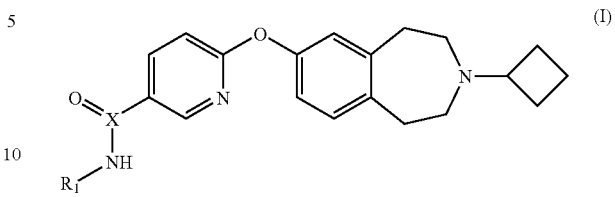

for use as an histamine $H_3$ ligand, wherein:

$R_1$ is a radiolabelled group incorporating or consisting of a radionuclide selected from $^3H$, $^{11}C$, $^{13}N$, $^{15}O$, $^{76}Br$, $^{18}F$, $^{123}I$, $^{125}I$, $^{131}I$, $^{75}Br$, $^{76}Br$, $^{77}Br$, $^{82}Br$ and X is C;

or $R_1$ is $C_{2-6}$alkyl and X is $^{11}C$;

or a pharmaceutically acceptable salt thereof.

In one embodiment a compound of formula (I) is [$^{11}C$-N-methyl]-6-(3-cyclobutyl-2,3,4,5-tetrahydro-1H-benzo[d] azepin-7-yloxy)-nicotamide (Compound A).

The present invention also provides a radiopharmaceutical composition which comprises a compound of formula (I) or [$^{11}C$-carbonyl] 6-(3-cyclobutyl-2,3,4,5-tetrahydro-1H-benzo[d]azepin-7-yloxy)-N-methylnicotamide and a pharmaceutically acceptable carrier or excipient.

The present invention also provides the use of a compound of formula (I) or [$^{11}C$-carbonyl] 6-(3-cyclobutyl-2,3,4,5-tetrahydro-1H-benzo[d]azepin-7-yloxy)-N-methylnicotamide for the manufacture of a medicament for the treatment or prophylaxis of neurological diseases including Alzheimer's disease, dementia, age-related memory dysfunction, mild cognitive impairment, cognitive deficit, epilepsy, neuropathic pain, inflammatory pain, migraine, Parkinson's disease, multiple sclerosis, stroke and sleep disorders including narcolepsy; psychiatric disorders including schizophrenia (particularly cognitive deficit of schizophrenia), attention deficit hyperactivity disorder, depression and addiction; and other diseases including obesity, asthma, allergic rhinitis, nasal congestion, chronic obstructive pulmonary disease and gastrointestinal disorders.

The present invention further provides a method for labelling histamine $H_3$ receptors in a mammal which comprises administering to a mammal an effective amount of a compound of formula (I) or [$^{11}C$-carbonyl] 6-(3-cyclobutyl-2,3, 4,5-tetrahydro-1H-benzo[d]azepin-7-yloxy)-N-methylnicotamide.

The present invention also provides a method for diagnostic imaging of histamine $H_3$ receptors in a mammal which comprises administering to a mammal an effective amount of a compound of formula (I) or [$^{11}C$-carbonyl] 6-(3-cyclobutyl-2,3,4,5-tetrahydro-1H-benzo[d]azepin-7-yloxy)-N-methylnicotamide.

The present invention also provides a method for diagnostic imaging of tissues expressing histamine $H_3$ receptors in a mammal which comprises administering to a mammal an effective amount of a compound of formula (I) or [$^{11}C$-carbonyl] 6-(3-cyclobutyl-2,3,4,5-tetrahydro-1H-benzo[d] azepin-7-yloxy)-N-methylnicotamide.

The present invention also provides a method for diagnostic imaging of histamine $H_3$ receptors in the brain of a mammal which comprises administering to a mammal an effective amount of a compound of formula (I) or [$^{11}C$-carbonyl] 6-(3-cyclobutyl-2,3,4,5-tetrahydro-1H-benzo[d]azepin-7-yloxy)-N-methylnicotamide.

The present invention further provides a method for the detection or quantification of histamine H₃ receptor functionality in mammalian tissue which comprises administering to a mammal in which such detection or quantification is desired an effective amount of a compound of formula (I) or [$^{11}$C-carbonyl] 6-(3-cyclobutyl-2,3,4,5-tetrahydro-1H-benzo[d]azepin-7-yloxy)-N-methylnicotamide.

Preferably, in the methods of the present invention the mammal is human.

The present invention also relates to a process for the preparation of [$^{11}$C-N-methyl]-6-(3-cyclobutyl-2,3,4,5-tetrahydro-1H-benzo[d]azepin-7-yloxy)-nicotamide which comprises reacting 6-(3-cyclobutyl-2,3,4,5-tetrahydro-1H-benzo[d]azepin-7-yloxy)-nicotamide with [$^{11}$C]methyl iodide.

Suitable radionuclides that may be incorporated in compounds of formula (I) include: $^{3}$H, $^{13}$N, $^{15}$O, $^{76}$Br, $^{18}$F, $^{123}$I, $^{125}$I, $^{131}$I, $^{75}$Br, $^{76}$Br, $^{77}$Br, $^{82}$Br and $^{211}$At. The choice of radionuclide to be incorporated into compounds of formula (I) will depend on the specific analytical or pharmaceutical application. Therefore, for in vitro labelling of histamine H3 receptors and for competition assays compounds that incorporate $^{3}$H, $^{125}$I or $^{77}$Br would be preferred. For diagnostic and investigative imaging agents, compounds that incorporate a radionuclide selected from $^{11}$C, $^{18}$F, $^{123}$I or $^{76}$Br are preferred. Incorporation of a chelating radionuclide may be useful in certain applications.

Radiolabelled analogues of compound (I) may be used in clinical studies to evaluate the role of histamine H₃ receptor ligands in a variety of disease areas where histamine H₃ receptor ligands are believed to be involved.

Scheme 1 represents a synthetic route towards compounds of formula (I) wherein R₁ is a radiolabelled group and R₁ is a leaving group.

Scheme 1

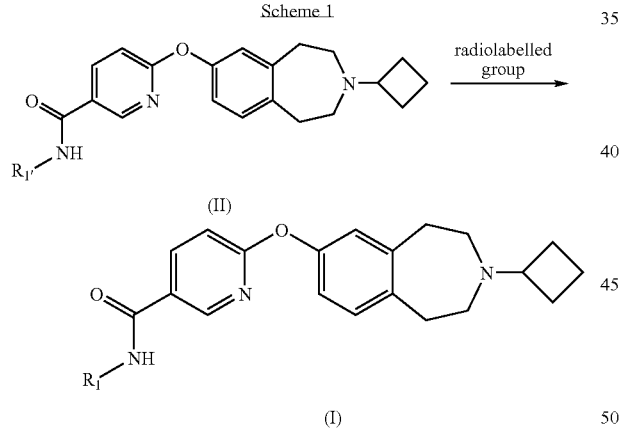

One synthetic route for the synthesis of a compound of formula (II) is shown in Scheme 2.

Scheme 2.

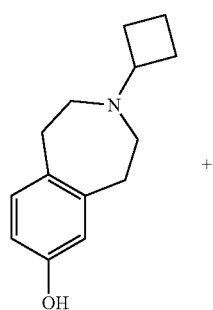

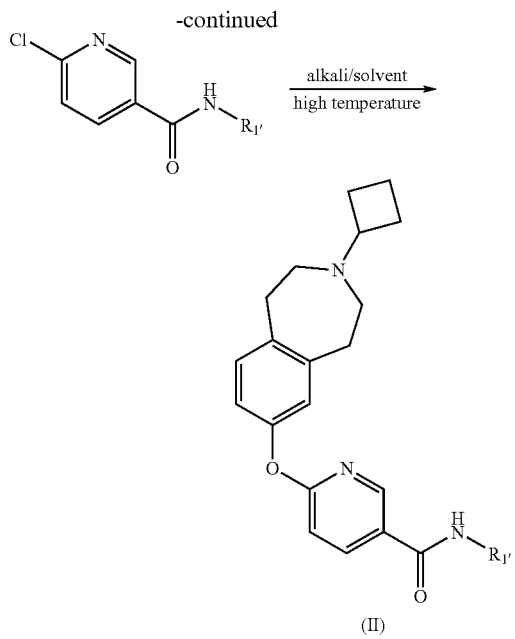

The starting materials and other reagents are available commercially or can be synthesised by well-known and conventional methods.

EXAMPLE 1

[$^{11}$C-N-methyl]-6-(3-cyclobutyl-2,3,4,5-tetrahydro-1H-benzo[d]azepin-7-yloxy)-nicotamide (Compound A)

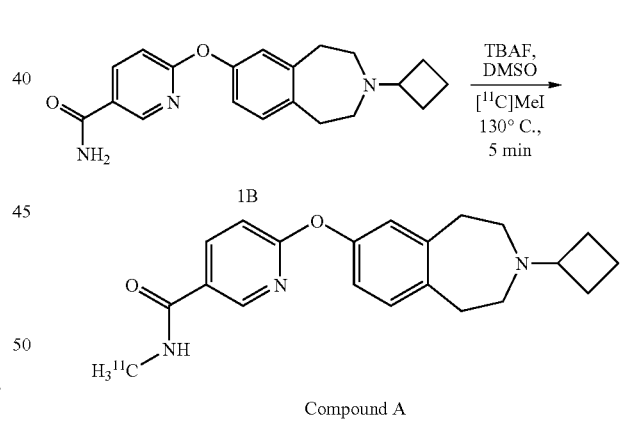

Compound A was prepared by N-alkylation of the carboxamide precursor 1B using cyclotron-produced [$^{11}$C]methyl iodide. Carbon-11 was produced as [$^{11}$C]CO₂ by bombarding nitrogen with 16.5 MeV protons according to the $^{14}$N(p,α) $^{11}$C reaction, the presence of a small amount of oxygen (0.5%) in the target gas converting the $^{11}$C into [$^{11}$C]CO₂. Subsequently, [$^{11}$C]CO₂ was converted into [$^{11}$C]MeI by catalytic reduction (Ni) which give the [$^{11}$C]CH₄ intermediate followed by gas phase iodination with iodine. The [$^{11}$C] methyl iodide was delivered to the reaction containing the precursor 1B and the tetrabutylammonium fluoride in dimethysulfoxide at room temperature. The reaction mix was heated at 130° C. for 5 min. Following a 70 min irradiation, typical syntheses provide 1.8 to 2.6 GBq of Compound A. For all the productions, the radiochemical purity was greater than 99% and the specific activity ranged from 260 to 1300 GBq/umol. The average total synthesis time including HPLC purification and formulation was approximately 40 min from the end of bombardment.

The precursor (1.0 mg) dissolved in dimethylsulfoxide (300 uL) was placed in a 1 mL glass vial. 20 uL of tetrabutylammonium fluoride were added. The [$^{11}$C]CH$_3$I was delivered as a gas to the reaction vial and bubbled through the solution containing the precursor at room temperature. After delivery of [$^{11}$C]CH$_3$I, the sealed vessel was heated at 130° C. for 5 min and injected onto the semi-prep HPLC column (Sphereclone ODS(2) C-18 250×10 mm). HPLC purification was performed at a 10 mL/min flow rate with a mobile phase consisting of acetonitrile and a solution of ammonium formate (50 mM) (42:58). The product fraction collected after approximately 7.7 min was evaporated to dryness and reformulated in 10 ml of 0.9% NaCl. Quality controls were performed on a Sphereclone ODS(2) C-18 250×4.6 mm using acetonitrile and a solution of ammonium formate (50 mM) (48:52) as mobile phase at a flow rate of 3 ml/min.

The present specification also describes the process for the preparation of [$^{11}$C-carbonyl] 6-(3-cyclobutyl-2,3,4,5-tetrahydro-1H-benzo[d]azepin-7-yloxy)-N-methylnicotamide (Compound B) by reacting 3-cyclobutyl-7-[(5-iodo-2-pyridinyl)oxy]-2,3,4,5-tetrahydro-1H-3-benzazepine with [$^{11}$C]BH$_3$.CO complex in presence of a palladium(0) catalyst (WO2005/014479).

EXAMPLE 2

[$^{11}$C-carbonyl] 6-(3-cyclobutyl-2,3,4,5-tetrahydro-1H-benzo[d]azepin-7-yloxy)-N-methylnicotamide (Compound B)

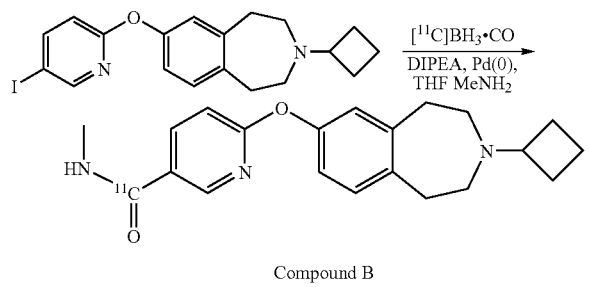

Compound B

[$^{11}$C]Carbon dioxide was produced by the $^{14}$N(p,α)$^{11}$C nuclear reaction using a nitrogen gas target (containing 1% oxygen) pressurised to 150 psi and bombarded with 16.5 MeV protons using the General Electric Medical Systems PETtrace 200 cyclotron. Typically, the irradiation time was 30 minutes using a 40 μA beam current. After irradiation, [$^{11}$C]carbon dioxide was trapped and concentrated on 4 Å molecular sieves. The trapped [$^{11}$C]CO$_2$ was released from molecular sieves in a stream of nitrogen (30 mL/min) by heating them to 350° C. [$^{11}$C]CO$_2$ was reduced on-line to [$^{11}$C]carbon monoxide after passing through a quartz tube filled with zinc granular heated to 400° C. The produced [$^{11}$C]CO was condensed onto a trap at −196° C. made from a 12-inch coil of 1/16" stainless steel tubing, 0.040" i.d., packed with carbonex 1000, 45/60 mesh (Supelco). After 6 min delivery and trapping of the [$^{11}$C]CO, the radioactive gas was then released at room temperature and carried out through an empty vial in a flow of nitrogen (6 mL/min) into a reactor loaded with the BH$_3$.THF solution (1.5 mL of a 1.0 M solution in THF) in order to form the [$^{11}$C]BH$_3$CO complex. The complex was then carried with the flow of nitrogen through an empty vial cooled at −78° C., and finally through the reaction vial cooled at −78° C. The reaction vial was prepared as follow: palladium(II) diacetate (0.5 mg, 0.0022 mmol) and triphenylphosphine (2.9 mg, 0.011 mmol) were dissolved in 400 μL of a solution of THF with 1% H$_2$O (degassed by bubbling N$_2$ through it for few minutes). Then, a mixture of 3-cyclobutyl-7-[(5-iodo-2-pyridinyl)oxy]-2,3,4,5-tetrahydro-1H-3-benzazepine (1.6 mg, 0.00365 mmol), DIPEA (1.53 μL, 0.0088 mmol) and methylamine 2.0 M (0.011 mmol, 5.48 μL solution in THF) were dissolved in 300 μL of THF with 1% H$_2$O (degassed by bubbling N$_2$ through it for 5 minutes) and added to the solution of the palladium complex. After trapping of the [$^{11}$C]BH$_3$.CO, the reaction mixture was heated at 140° C. for 8 min, filtered and analysed for radioactivity content. The analysis of the HPLC chromatograms showed the formation of the desired [$^{11}$C-carbonyl] 6-[(3-cyclobutyl-2,3,4,5-tetrahydro-1H-3-benzo[d]azepin-7-yl)oxy]-N-methylnicotinamide in approximately 44% yield.

Biological Data

1. In vitro Activity

The in vitro affinity of unlabelled Compound A for the histamine H$_3$ receptor was determined by competition assay using [$^{125}$I]iodoproxifan as radioligand binding to cell lines stably expressing human histamine H$_3$ receptor.[13]

Unlabelled Compound A showed a very high affinity for the human histamine H$_3$ receptor with a pKi value of 9.59 and a high selective over other receptors.

TABLE 1

| Binding affinity (pKi) of unlabelled compound A | | | | |
| --- | --- | --- | --- | --- |
| Human receptor | H$_3$ | H$_1$ | H$_2$ | H$_4$ |
| pKi | 9.59 | 5.6 | <5.5 | <5.5 |

2. In vivo Imaging 2.1 PET Imaging with Compound A

The animals (pig, Yorkshire/Danish Landrace (~40 Kg; n=2) were housed singly in thermostatically controlled (20° C.) and naturally illuminated stalls. They were scanned under terminal anaesthesia (ketamine induced isoflurane anaesthesia) on different days. The left femoral artery and vein of each animal were surgically cannulated using catheters (Avanti® size 4F-7F). Blood samples were collected from the femoral artery and the radiolabelled and non-labelled agents were injected to the femoral vein. Animals were placed supine in a Siemens ECAT EXACT HR tomograph, with the head immobilized in a custom-made holding device. During the study, blood pH, pCO$_2$ and pO$_2$ levels were monitored and maintained within the normal physiological range. In addition, BP and heart rate were recorded throughout the study. Compound A was administered intravenously in the femoral vein as a 1 minute bolus injection. PET scanning and arterial blood sampling was commenced upon start of the radioligand administration.

PET images were acquired from 0 to 90 min following administration of Compound A. Compound A readily enters the pig brain; the radioactivity reached its peak uptake at 25 min after administration of the radiotracer and then steadily declined over the remainder of the study. The regional brain distribution of Compound A reflected the known distribution of the histamine $H_3$ receptor with a higher accumulation in the striatum, cortices, thalamus and hypothalamus. Compound A concentration was low in cerebellum, a brain region known to possess very low level of $H_3$ receptors. The highest ratios relative to cerebellum occurred at the end of the study (85 min) and were 9.0, 5.3, 4.9, 3.8 and 3.4 for the striatum, frontal cortex, parietal cortex, occipital cortex and thalamus respectively.

2.2 PET Imaging with Pharmacological Challenges

Four sequential high specific activity iv radioligand Compound A administrations were performed in same animal, same day. Following a baseline scan, Compound A was co-administered with escalating dose of unlabelled unlabelled compound A (0.005, 0.05 and 0.5 mg/kg). [$^{15}$O]CO and [$^{15}$O]$H_2O$ were administered pre and post administration of unlabelled compound A to monitor and to correct for changes in cerebral blood volume and changes in cerebral blood flow. Following administration of unlabelled compound A, the specific uptake of radiotracer was blocked leading to a homogenous distribution of radioactivity throughout the brain. A similar experiment was performed using escalating dose of ciproxifan (0.006, 0.06, 0.6 and 2.0 mg/kg), a known selective histamine $H_3$ antagonist. A dose-dependent decrease of compound A uptake in the $H_3$-rich regions of the brain was observed. When 2.0 mg/kg of ciproxifan was administered, the ratios tissue to cerebellum reached 1.22, 1.08, 0.99, 0.91 and 0.72 for the striatum, frontal cortex, occipital cortex, parietal cortex and thalamus respectively at 85 min post-injection.

What is claimed is:

1. [$^{11}$C-N-methyl]6-(3-cyclobutyl-2,3,4,5-tetrahydro-1H-benzo[d]azepin-7-yloxy)-nicotamide.

2. A pharmaceutical composition which comprises a compound according to claim 1.

3. A method for labelling histamine $H_3$ receptors in a mammal which comprises administering to a mammal an effective amount of a compound according to claim 1.

4. A method according to claim 3 which additionally comprises detection of the labelled histamine $H_3$ receptors by positron emission tomography.

5. A method for diagnostic imaging of histamine $H_3$ receptors which comprises administering to a mammal an effective amount of a compound according to claim 1.

* * * * *